US007829110B2

(12) United States Patent
Wohlert

(10) Patent No.: US 7,829,110 B2
(45) Date of Patent: Nov. 9, 2010

(54) SURGICAL IMPLANT COMPRISING AN ANABOLIC AND A CORTICOSTEROID

(75) Inventor: Stephen Wohlert, Norderstedt (DE)

(73) Assignee: Ethicon, Inc., Somerville, NJ (US)

( * ) Notice: Subject to any disclaimer, the term of this patent is extended or adjusted under 35 U.S.C. 154(b) by 1065 days.

(21) Appl. No.: 10/545,112

(22) PCT Filed: Feb. 6, 2004

(86) PCT No.: PCT/EP2004/001113

§ 371 (c)(1),
(2), (4) Date: Aug. 10, 2005

(87) PCT Pub. No.: WO2004/071485

PCT Pub. Date: Aug. 26, 2004

(65) Prior Publication Data

US 2006/0147488 A1    Jul. 6, 2006

(30) Foreign Application Priority Data

Feb. 12, 2003   (DE)   ................................ 103 05 811

(51) Int. Cl.
*A61F 2/00*   (2006.01)
(52) U.S. Cl. ..................................................... 424/423
(58) Field of Classification Search ................ 424/423; 604/891.1, 28, 198
See application file for complete search history.

(56) References Cited

U.S. PATENT DOCUMENTS

| | | | | |
|---|---|---|---|---|
| 5,342,348 A * | 8/1994 | Kaplan | ..................... | 604/891.1 |
| 5,569,678 A | 10/1996 | Lee | | |
| 5,707,647 A * | 1/1998 | Dunn et al. | .................. | 424/443 |
| 5,780,050 A * | 7/1998 | Jain et al. | .................... | 424/449 |
| 6,306,426 B1 * | 10/2001 | Olejnik et al. | .............. | 424/426 |
| 6,537,565 B2 * | 3/2003 | Swanbom et al. | ........... | 424/402 |
| 2002/0071855 A1 | 6/2002 | Sadozai et al. | | |
| 2003/0105245 A1 * | 6/2003 | Amsden | ..................... | 525/450 |
| 2003/0147936 A1 | 8/2003 | Sahadevan | | |

FOREIGN PATENT DOCUMENTS

| | | |
|---|---|---|
| GB | 1420831 A | 1/1976 |
| WO | WO 02/09792 A1 | 2/2002 |
| WO | WO 0226109 A2 * | 4/2002 |
| WO | WO 02/36054 A1 | 5/2002 |

OTHER PUBLICATIONS

Ehrlich, H. Paul et al. "The Effects of Cortisone and Anabolic Steroids on the Tensile Strength of Healing Wounds", Annals of Surgery, 1969, pp. 203-206.*
Klosterhalfen, B. et al. "Influence of implantation interval on the long-term biocompatibility of surgical mesh", Brit. J. Surg., 89, 202, 1043-1048.
Klinge, U. et al., "Foreign Body Reaction to Meshes Used for the Repair of Abdominal Wall Hernias", Eur. J. Surg., 165, 1999, 665-673.
Jenney, C.R., et al., "Effects of surface-coupled polyethylene oxide on human macrophage adhesion and foreign body giant cell formation in vitro", J. Biomed. Mater. Res., 44(2), 1999, 202-216.
Matsuda, S. et al., "Evaluation of the antiadhesion potential of UV cross-linked gelatin films in a rat abdominal model", Biomaterials 23, 202, 2901-2908.
O'Kane, S. et al., "Transforming Growth Factor βs and Wound Healing", Int. J. Biochem. Cell Biol., 29(1), 1997, 63-78.
Dixon, M.J.. "The Effects of Epidermal Growth Factor, Transforming Growth Factors Alpha and Beta and Platelet-Derived Growth Factor on Murine Palatal Shelves in Organ Culture", Archs. Oral. Biol., 37 (5), 1992, 395-410.
Saarela, T. et al., "Effect of short-term antenatal dexamethasone administration on type I collagen synthesis and degradation in preterm infants at birth", Acta Paediatr., 90 (8), 2001, 921-925.
Czarnetzki, B.M., "Vitamin D3 in Dermatology: A Critical Appraisal, Dermatologica", 178 (4), 1989, 184-188.
Greiling, D. et al., "1α,25-Dihydroxyvitamin D3 Rapidly Inhibits Fibroblast-Induced Collagen Gel Contraction", J. Invest. Dermatol., 106 (6), 1996, 1236-1241.
Falanga, V. et al., "Stimulation of Collagen Synthesis by the Anabolic Steroid Stanozolol", J. Invest. Dermatol., 111 (6), 1998, 1193-1197.
Demling, R. H. "Oxandrolone, an anabolic steroid, enhances the healing of a cutaneous would in the rat", Wound Rep. Reg., 8 (2), 2000, 97-102.
Hatz, R. A. et al., "The Tetrachlordecaoxygen Complex Reverses the Effect of Cortisone on Wound Healing", Plast. Reconstr. Surg., 84 (6), 1989, 953-959.
Kim, C.S. et al., "The Effect of Anabolic Steroids on Ameliorating the Adverse Effect of Chronic Corticosteroids on Intestinal Anastomotic Healing in Rabbits", Surg. Gynecol. Obstet. 176 (1), 1993, 3-79.
Matsumoto, J. et al., "Preparation of nanoparticles consisted of poly(L-lactide)-poly(ethylene glycol)-poly(L-lactide) and their evaluation in vitro", Int. J. Pharm. 185 (1), 1999, 93-101.
Anstead, G. M., "Steroids, Retinoids, and Wound Healing", Advances in Wound Care, pp. 277-285 (1998).
Van Story-Lewis, P. E. et al., "Glucocorticoid Inhibition of Fibroblast Contraction of Collagen Gels", Biochemical Pharmacology, vol. 35, No. 8, pp. 1283-1286 (1986).
Chong S. Kim et al.: The effect of anabolic steroids on ameliorating the adverse effects of chronic corticosteroids on intestinal anastomotic healing in rabbits. Surgery Gynecology and Obstetrics 176(1), 1993,73-79.

* cited by examiner

*Primary Examiner*—Robert A Wax
*Assistant Examiner*—Suezu Ellis
(74) *Attorney, Agent, or Firm*—Roberts Mlotkowski Safran & Cole, P.C.

(57) ABSTRACT

A surgical implant with a basic structure, preferably configured as an implant mesh, contains an anabolic steroid and a corticosteroid. The implant is preferably designed to release these active substances after implantation. It becomes incorporated rapidly and effectively, without any undesired scar contraction occurring.

6 Claims, No Drawings

SURGICAL IMPLANT COMPRISING AN ANABOLIC AND A CORTICOSTEROID

CROSS-REFRENCE TO RELATED APPLICATIONS

This application is a National Stage application under 35 U.S.C. 371 of PCT/EP2004/001113, filed 06 Feb. 2004, which claims priority from DE10305811.7filed 12 Feb. 2003.

The invention relates to a surgical implant (in particular an implant mesh) which, while permitting accelerated wound-healing, does not additionally cause scar contraction.

After they have been implanted in the body, implants generate a foreign-body reaction which, following an inflammatory reaction, leads to the formation of scar tissue. The foreign-body reaction triggers a formation of connective tissue around the implant, and, at a later stage, this connective tissue further differentiates to a greater or lesser extent into scar tissue. Scar tissue is tighter than connective tissue, which means that, in the course of said differentiation, the tissue draws together and the implant thus also contracts.

In the case of incisional hernias, a reduction of up to 80% in the surface area of the implant is observed in the course of wound-healing. This "shrinkage" is due to the contraction of the formed scar tissue around the implant. The reduction in the surface area of an implant mesh can lead to recurrences, particularly in the case of hernias.

The contraction depends on the quantity of implant used (pore width in the case of meshes, weight) and on the surface characteristics of implant. The shrinkage observed in conventional polypropylene meshes is usually between 30% and 50% of the original surface area (Klosterhalfen, B., Junge, K., Hermanns, B., Klinge, U.: Influence of implantation interval on the long-term biocompatibility of surgical meshes, Brit,. J. Surg., 89, 2002, 1043-1048; Klinge, U., Klosterhalfen, B., Müller, M., Schumpelik, V.: Foreign body reaction to meshes used for the repair of abdominal wall hernias, Eur. J. Surg., 165, 1999, 665-673), in ePTFE meshes it is 30% to 50% (Klinge, U., Klosterhalfen, B., Müller, M., Schumpelik, V.: Foreign body reaction to meshes used for the repair of abdominal wall hernias, Eur. J. Surg., 165, 1999, 665-673), and in the partially resorbable composite meshes sold by Ethicon, under the names "Vypro" and "Vypro II", it is about 30% (Klinge, U., Klosterhalfen, B., Müller, M., Schumpelik, V.: Foreign body reaction to meshes used for the repair of abdominal wall hernias, Eur. J. Surg., 165, 1999, 665-673) and under 10%, respectively.

Various approaches are known for reducing the foreign-body reaction:

Changing the geometry of the mesh to give a smaller surface area (hence fewer foreign bodies), for example by using monolfilaments or larger pores (V. Schumpelik, Hernien, published by Thieme Verlag, 4th edition, 1992, 10-11). Thus, conventional polypropylene meshes have narrow pores and a large weight per unit area, while the abovementioned "Vypro" meshes are partially resorbable and have wide pores in the non-resorbable area.

Modifying the surface of the implant material, for example modification by physical methods (Plasma, Plasma polymerization; B. Ratner (Ed.), Biomaterials science, an introduction to materials science, 105 et seq.), modification by chemical methods (B. Ratner (Ed.), Biomaterials science, an introduction to materials science, 105 et seq.), for example with PEO (Jenney, C. R., Anderson, J. M.: Effects of surface-coupled PEO on human macrophage adhesion and foreign body giant cell formation in vitro, J. Biomed. Mater. Res., 44(2), 1999, 202-216), PVA (Matsuda, S. Se, N., Iwata, H., Ikeda, Y.: Evaluation of the antiadhesion potential of UV cross-linked gelatin films in a rat abdominal model, Biomaterials 23(14), 2002, 2901-2908); US 2002/0071855, hyaluronic acid (WO 02/09792 A1) or by graft copolymerization (directly or after activation) (B. Ratner (Ed.), Biomaterials science, an Introduction to materials science, 105 et seq.), and modification by coating the implant with a biocompatible layer, for example by dip coating or spin coating.

Using what are called active implants (Drug Delivery Systems) in which biologically active molecules are incorporated into the implant, for example TGF-beta (O'Kane, S., Ferguson, M. W. J.: TGF-beta in wound healing, Int. J. Biochem. Cell Biol., 29(1), 1997, 63-78) or TGF-alpha (Dixon, Fergusson: The effects of EGF, TGF-alpha, TGF-beta, PDGF on murine palatal shelves in organ culture, Arch. Oral. Biol., 37(5), 1992, 395-410). Such implants release agents and are aimed at controlling the connective tissue in a specific and oriented manner around the implant and at generally reducing the foreign-body reaction, in order thereby to counteract contraction.

It is known that corticcsteroids such as dexamethasone (Saarela, T., Risteli, J., Kauppila, A., Koivisto, M.: Effect of short term antenetal dexamethasone administration on type I collagen synthesis and degradation in preterm infants at birth, Acta Pediatr., 90(8), 2001, 921-925) inhibit the synthesis of type I collagen and thus of stable connective tissue (Anstead: Steroids, retinoids and wound healing, Adv. Wound Care, 11(6), 1998, 277-285); at fairly high dosages the same applies to vitamin D3 and its derivatives (Czarnetzki, B. M.: Vitamin D3 in dermatology: a critical appraisal, Dermatologica, 178 (4), 1989, 184-188). In addition, they inhibit the contraction of type I collagen in the course of wound-healing (Greiling, D.: 1-alpha-25dihydroxyvitamin D3 rapidly inhibits fibroblast induced collagen gel contraction, J. Invest. Dermatol., 106(6), 1996, 1236-1241; Van Story-Lewis, P. E., Tenenbaum, H. C.: Glucocorticoid inhibition of fibroblast contraction of collagen gels, Biochem. Pharmacol., 35(8), 1986, 1283-1286). Anabolic steroids, by contrast, increase the synthesis of type I collagen (Falanga, V., Greenberg, A. S., Zhou, L., Ochoa, S. M., Roberts, A. B., Falabella, A., Yamaguchi, Y.: Stimulation of collagen synthesis by the anabolic steroid stanozolol, J. Invest. Dermatol., 111(6), 1998, 1193-1197; Demling, R. H.: Oxandrolone, an anabolic steroid, enhances the healing of a cutaneous wound in the rat, Wound Rep. Regen., 8(2), 2000 97-102).

A combination of corticosteroids and anabolic steroids leads to increased collagen production without simultaneous wound contraction (Hatz, Kelley, Ehrlich: The tetrachlordecaoxygen complex reverses the effect of cortisone on wound healing, Plast. Reconstr. Surg., 84(6), 1989, 953-959; Kim, C. S. et al.: The effect of anabolic steroids on ameliorating the adverse effect of chronic corticosteroids on intestinal anestototic healing in rabbits, Surg. Gynecol. Obstet. 176(1), 1993, 73-79).

Corticosteroids are also used as immunosuppressants, and anabolic steroids for building muscle and in the treatment of osteoporosis.

The object of the invention is to make available a surgical implant which becomes incorporated rapidly and effectively but which does not cause undesired scar contraction.

This object is achieved by a surgical implant with the features of claim 1. Advantageous embodiments of the invention are set out in the dependent claims.

The surgical implant according to the invention has a basic structure and comprises (at least) one anabolic steroid and (at least) one corticosteroid. The basic structure is preferably designed with an areal configuration, and specifically preferably as an implant mesh, although it can also be in another form (see below). The implant is preferably designed to release the anabolic steroid and/or the corticosteroid after implantation.

With the implant according to the invention, it is possible, in addition to the primary support function of the implant, to achieve a local administration of two active substances, namely an anabolic steroid and a corticosteroid, which act directly on the surrounding tissue. The anabolic steroid increases and accelerates the formation of type I collagen (synthesis of support tissue). The corticosteroid prevents the contraction of the support tissue as this matures to scar tissue. Thus, firmer integration (more collagen) of the basic structure of the implant is achieved without contraction. The implant thus becomes rapidly incorporated without reduction of its surface area. The accelerated and firmer incorporation, without scar contraction, reduces the risk of recurrence.

The anabolic steroid and the corticosteroid exert a local action. It is thus possible to avoid the side effects which can arise in systemic administration. After implantation, the implant according to the invention can release the anabolic steroid and/or the corticosteroid either immediately or after a delay, and the release can also take place over a long period of time. In this way, the stated effects are induced in the region of the implant. The time pattern of the release of the steroids can be predetermined by the way in which they are arranged in or on the basic structure. For example, the steroids can diffuse relatively quickly out of the pores of the basic structure if they are bound only in the surface of the latter via intermolecular forces. If, by contrast, the steroids are located in the inside of a resorbable polymer, the time of release depends on the progress of the resorption of the polymer.

The quantity of anabolic steroid and of corticosteroid in the implant according to the invention (expressed as absolute mass or in percent by weight relative to the weight of the basic structure) can vary over a wide range, depending on the specific application, and can be determined specifically for the particular case. For the anabolic steroid, data from systemic use may serve as a starting point. For example, depending on the steroid, administrations of between 0.5 μg/kg/day (fluoxymesterone) through 0.1 to 3 mg/kg/day (tibolone) up to 10 mg/kg/day (testosterone) for prolonged periods (here in each case related to 1 kg bodyweight) or, for example, individual intramuscular injections of 50 mg are known. For stanozolol, the natural serum level (plasma level) is approximately $10^{-8}$ M and the toxic dose is $10^{-4}$ M; in this case the practical dose range extends from approximately $10^{-8}$ M to approximately $10^{-5}$ M. For glucocorticoids, individual systemic doses of 10 mg/kg/day and local doses in the wound area of 2 μg/day to 50 mg/day (depending on the preparation) are known. When transposing the systemic dose ranges to the implant, account must be taken of the local area of action (i.e. the lower weight of the body tissue in question) and the generally higher tolerance at the desired site of action.

For the basic structure, which largely determines the mechanical properties of the implant, very different forms can be considered depending on the intended use. Apart from the areal implant structures already Mentioned (in particular implant meshes, preferably for treatment of hernias), other examples are: three-dimensional structures, fleece-like structures, felts, blocks, porous structures, foams, cords, threads, and tapes, but also, for example, vessel prostheses end stents. Not least, combinations or composites of the aforementioned forms are also possible.

The basic structure can be resorbable, non-resorbable or partially resorbable. It can include inorganic and/or organic material. Examples of inorganic materials are: hydroxylapatite, calcium phosphates (e.g. dicalcium phosphate and octacalcium phosphate, but in particular tricalcium phcsphate and its modifications such as alpha-tricalcium phosphate and beta-tricalcium phosphate), mixed phosphates, non-resorbable glasses and resorbable glasses. So-called biological glasses of varying composition may also be considered. Examples of organic materials are: polymers (non-resorbable or resorbable), reinforced polymers, pre-degraded resorbable polymers (e.g. a copolymer of glycolide and lactide in the ratio 90:10, whose duration of resorption is shortened by pretreatment in a hydrolysis buffer), polylactides (e.g. poly-L-lactides and poly-D-lactides), polyglycolides, copolymers of glycolides and lactides, poly-p-dioxanone and polycaprolactones, but also natural polymers such as celluloses (e.g. alginate, starch and derivatives thereof). The basic structure can, in principle, comprise several different materials.

For the anabolic steroid, examples which may be considered are tibolone, fluoxymesterone, stanozolol, nandrolone, nancrolone decanoate, nandrolone octydecanoate, and testosterone, and derivatives of these substances. It is also conceivable to provide more than one anabolic steroid so that the actions of the individual steroids can complement each other.

Examples of corticosteroid are: cortisone, furacin, polysporin, methylprednisolone, dexamethasone and glucocorticoids. If necessary, a plurality of corticosteroids can be provided.

There are a great many possible ways of integrating the anabolic steroid and the corticosteroid into the basic structure or of arranging them on top of the latter and, if appropriate, of connecting them to the basic structure, optionally also so that the steroids are released in a chronologically predetermined manner. For example, the steroids can be included in a coating of the basic structure. If the coating comprises a resorbable basic substance, the steroids are released in the course of the resorption process. Moreover, a steroid can be contained in the inside of the basic structure, for example in a basic structure made of resorbable material. The release of active substances from spheres is described in the literature (e.g. Matsumoto, J., Nacada, Y., Sakurai, K., Nakamura, T., Takahashi, Y.: Preparation of nanoparticles consisting of poly(L-lactide)-poly(ethylene glycol)-poly(L-lactide) and their evaluation in vitro, Int. J. Pharm., 185(1), 1999, 93-101).

Coatings with the anabolic steroid and/or the corticosteroid can be applied to the basic structure by spraying or by means of an immersion process, for example. If a steroid is to be introduced in the inside of the basic structure, suitable processes are, for example, swelling in a solvent with the steroid, diffusion processes, immersion processes (with a porous basic structure), shaping of the basic structure from a steroid-containing melt, and use of emulsions or supercriticial carbon dioxide.

The anabolic steroid and/or corticosteroid can also be contained in a release unit arranged or the basic structure, for example in a pellet with a resorbable material as binder. Several coatings are also conceivable, e.g. including separate coatings for the individual active substances, or combined forms of the possibilities mentioned. These individual variations care be used to influence or control the local action and timing of the steroids.

The invention is explained in more detail below on the basis of examples.

EXAMPLE 1

An anabolic steroid and a corticosteroid are dissolved in a coating solution. A commercially available implant mesh for hernia repair is immersed in a bath containing this solution and then removed from the latter. After drying, the active substances remain in the surface of the implant mesh serving as basic structure. After implantation of the mesh, the active substances are released and thereby exert their intended effect.

EXAMPLE 2

For a trial on rabbits, dexamethasone (0.1 mg/kg) and nandrolone (2 mg/kg to 20 mg/kg) are combined in different ratios in a controlled-release pellet made of a resorbable lactide/glycolide copolymer. When implanted on a wound, this leads to accelerated wound-healing with reduced wound contraction but the same stability of the wound (tear resistance of the newly formed skin). The pellet is suitable for integration into an implant.

EXAMPLE 3

A hernia mesh charged with anabolic steroid and corticosteroid as active substance is introduced using one of the standerd open or laparoscopic techniques and thus actively supports the healing of the defect in addition to the stabilizing action of the implant mesh per se. All applications in contact with soft tissue are conceivable.

EXAMPLE 4

Stanozolol (0.5 µg/ml to 5 µg/ml) increases the synthesis of type I collagen in human skin fibroblasts by a factor of 2 to 4.
Cortisone prevents fibroblast contraction (human, dermal) even at low doses (below $10^{-6}$ M)

EXAMPLE 5

A combination of cortisone and testosterone in a controlled-release pellet accelerates wound-healing while maintaining the tear resistance of the newly formed tissue, even in immunosuppressed rats.

EXAMPLE 6

To test a hernia mesh for preventing scar contraction, a tube made of colorless "Vicryl" yarn ("Vicryl": copolymer of glycolide and lactide in the ratio of 90:10, Ethicon, Germany) of 56 dpf (deniers per filament) with a diameter of 10 mm is produced on a Lucas circular knitting machine.
This tube is coated in one stage by completely immersing it for about 2 minutes in a bath containing the following:
  5% by weight of glycolide/lactide copolymer (35% by weight of glycolide, 65% by weight of lactide) with an intrinsic viscosity of 0.4 dl/g to 0.8 dl/g
  10% by weight of nandrolone
  1% by weight of dexamethasone
  dispersed in ethyl acetate (remainder % by weight)
The tube is then dried at 50° C. to 55° C. The coated tube is stored in a nitrogen atmosphere.
Efficacy is demonstrated in the rat model. Pieces measuring 1 cm in width and 5 cm in length are cut out from the tube and implanted under the skin of a rat's back and then explanted after 7, 14, 21, 56 and 119 days. After explantation, the remaining surface area of the respective piece is measured and the resulting scar tissue is tested for its tear resistance and type I collagen content. Pieces of uncoated "Vicryl" tube and an uncoated "Vicryl" mesh ("Type 9," Ethicon, fine-pore mesh) are used as control. The quantity of newly formed type I collagen in the coated pieces is twice the quantity in the control. As a result, the tear resistance of the tissue also increases, with significantly less scar contraction (measured on the basis or the remaining surface area of the respective piece).

EXAMPLE 7

In a two-stage process, a first coating with steroid (in this case stanozolol and cortisone) is applied to an uncoated "Vicryl" mesh analogously to Example 6. After drying, an additional layer is added of the coating polymer, (without steroid). The active substances are therefore located farther away from the surface, so that after implantation they are retardedly released in the course of the resorption of the coatings.

EXAMPLE 8

Analogously to the tubers described in Example 6, a great many other basic structures can be equipped in the ways described In Examples 6 and 7, for example:
  meshes made of "Vicryl" (copolymer of glycolide and lactide in the ratio 90:10, Ethicon),
  meshes made of "Vypro" (composite of "Vicryl" and polypropylene, Ethicon),
  composite meshes mace of "Vicryl" and "Proncva" ("Pronova": mixture of polyvinylidene fluoride and a copolymer of vinylidene fluoride and hexafluoropropene, Ethicon),
  "Mersilene" meshes (polyester, Ethicon),
  "Monocryl"-containing meshes (copolymer of glycolide and epsilon-caprolactone, Ethicon),
  mesh pouches made of "Vicryl",
  and other non-resorbable meshes,
  tapes and cords, for example a woven polyester tape ("Mersilene", Ethicon) or made of other resorbable and non-resorbable materials,
  fleeces, needlefelts and felts made of "Vicryl" and/or poly-p-dioxanone yarns,
  vessel prostheses,
  stents.

The invention claimed is:
1. A method of increasing tear resistance of scar tissue during wound repair comprising:
  applying to a wound a surgical mesh comprising an anabolic steroid and a corticosteroid disposed in or on a surgical mesh structure.
2. The method according to claim 1, further comprising at least one of the substances selected from the group consisting of hydroxylapatite, calcium phosphates, non-resorbable glasses, resorbable glasses, polymers, resorbable polymers, reinforced polymers, pre-degraded resorbable polymers, polylactides, poly-L-lactides, poly-D-lactides, polyglycolides, copolymers of glycolides and lactides, poly-p-dioxanone, polycaprolactones, and celluloses.
3. The method according to claim 1, wherein the anabolic steroid comprises at least one of the substances selected from the group consisting of stanozolol, nandrolone, nandrolone decanoate, nandrolone octydecanoate, testosterone, tibolone, fluoxymesterone, and derivatives of the aforementioned substances.

4. The method according to claim 1, wherein the corticosteroid comprises at least one of the substances selected from the group consisting of cortisone, furacin, polysporin, methylprednisolone, dexamethasone, and glucocorticoids.

5. The method according to claim 1, wherein at least one of the anabolic steroid and corticosteroid is contained in at least one coating on the surgical mesh.

6. The method according to claim 1, wherein at least one of the anabolic steroid and corticosteroid is contained in a release unit arranged on the surgical mesh.

* * * * *